United States Patent [19]
Scott et al.

[11] Patent Number: 5,559,260
[45] Date of Patent: Sep. 24, 1996

[54] PRECURSORS AND PROCESSES FOR MAKING METAL OXIDES

[75] Inventors: Michael C. Scott; Carlos A. Paz de Araujo; Larry D. McMillan, all of Colorado Springs, Colo.

[73] Assignee: Symetrix Corporation, Colorado Springs, Colo.

[21] Appl. No.: 477,068

[22] Filed: Jun. 7, 1995

Related U.S. Application Data

[63] Continuation-in-part of Ser. No. 132,744, Oct. 6, 1993, Pat. No. 5,514,822, which is a continuation-in-part of Ser. No. 993,380, Dec. 18, 1992, Pat. No. 5,456,945, Ser. No. 981,133, Nov. 24, 1992, Pat. No. 5,423,285, and Ser. No. 965,190, Oct. 23, 1992, abandoned, said Ser. No. 981,133, and Ser. No. 965,190, each is a continuation-in-part of Ser. No. 807,439, Dec. 13, 1991, abandoned.

[51] Int. Cl.$^6$ ................................. C07F 5/00; C07F 7/22
[52] U.S. Cl. .................. 556/28; 556/1; 556/31; 534/16
[58] Field of Search ................. 556/28, 31, 1; 534/16

[56] References Cited

U.S. PATENT DOCUMENTS

| | | | |
|---|---|---|---|
| 3,647,364 | 3/1972 | Mazdiyasni et al. | 23/51 |
| 5,028,455 | 7/1991 | Miller et al. | 427/126.3 |
| 5,034,550 | 7/1991 | Sherif | 556/54 |
| 5,122,923 | 6/1992 | Matsubara et al. | 361/321 |

FOREIGN PATENT DOCUMENTS

| | | |
|---|---|---|
| 0125507 | 4/1984 | European Pat. Off. . |
| 0344567 | 5/1989 | European Pat. Off. . |
| 59-042392 | 3/1984 | Japan . |

OTHER PUBLICATIONS

Chandler, Clive D. and Hampden-Smith, Mark J.; Formation of Crystalline, Integral, and Nonintegral Stoichiometry Perovskite-Phase Complex Metal Oxide Powders from Metal-Organic Precursors; Chemistry of Materials, 1992, Nov./Dec., No. 6, Washington, DC, US.

W. W. Davison, S. G. Shyu, R. D. Roseman & R. C. Buchanan, "Metal Oxide Films From Carboxylate Precursors", Mat. Res. Soc. Symp. Proc., vol. 120, pp. 179–402 (1988).

K. Koyama, T. Sakuma, S. Yamamichi, H. Watanabe, H. Aoki, S. Ohya, Y. Miyasaka & T. Kikkawa, "A Stacked Capacitor with $(Ba_xSr_{1x})TiO_3$ for 256M Dram" IEDM (Dec. 1991).

P. C. Joshi, A. Mansingh, M. N. Kamalasanan & S. Chandra "Structural & Optical Properties of Ferroelectric $Bi_4Ti_3O_{12}$ Thin Films by Sol–Gel Technique". Aug. 12, 1991.

G. M. Vest & Singaram, "Synthesis of Metallo-Organic Compounds for Mod Powders and Films," Mat. Res. Soc. Symp. Proc., vol. 60, pp. 35–42 (1986).

B. M. Melnick, J. D. Cuchiaro, L. D. McMillian, C. A. Paz de Araujo & J. F. Scott, "Process Optimization & Characterization of Device Worthy Sol–gel Based PZT for Ferroelectric Memories." Nov. 20, 1989.

J. V. Mantese, A. L. Micheli, A. H. Hamdi & R. W. Vest "Metalorganic Deposition (MOD): A Nonvacuum, Spin-on, Liquid-Based, Thin Film Method, " (1989).

*Primary Examiner*—Porfirio Nazario-Gonzales
*Attorney, Agent, or Firm*—Duft, Graziano & Forest, P.C.

[57] ABSTRACT

A precursor is made by mixing a metal alkoxycarboxylate-containing liquid with a 2-ethylhexanoic acid in an effective amount for shelf-stabilizing said liquid by substituting 2-ethylhexanoate ligands for alkoxide ligands, thereby forming a mixture, and heating said mixture to substitute said carboxylate ligands for said alkoxide ligands. Specfically, a barium strontium titanate precursor and a strontium bismuth tantalate precursor are made by combining polyoxyalkylated metal moieties to form a liquid solution in which the metal atoms bond with an oxygen atom in a ligand selected from a ligand group consisting of alkoxides and carboxylates, then then heating the liquid solution.

17 Claims, 4 Drawing Sheets

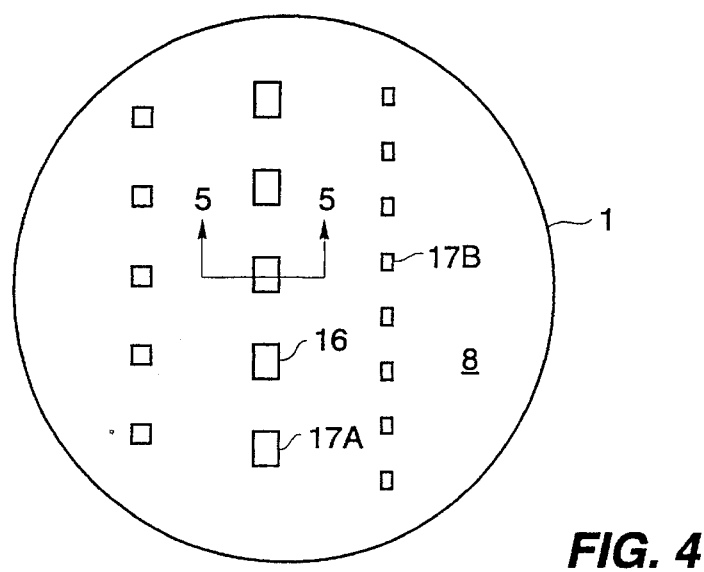
FIG. 4
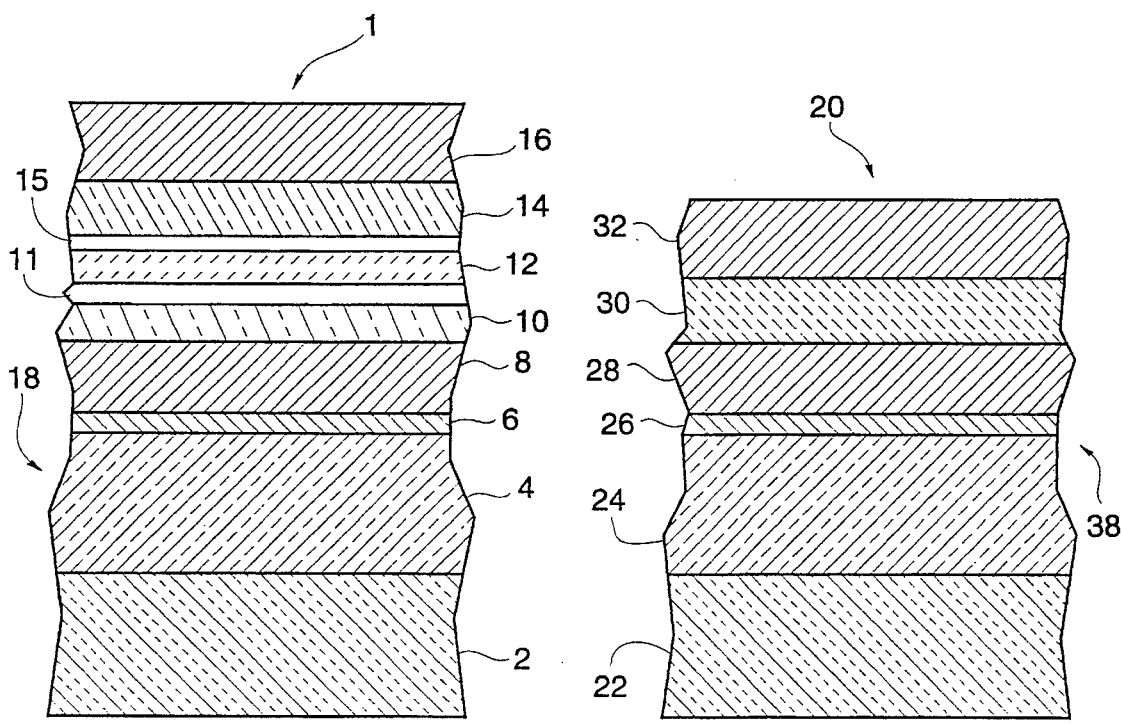
FIG. 5  FIG. 6

PRECURSORS AND PROCESSES FOR MAKING METAL OXIDES

This application is a continuation-in-part of U.S. patent application Ser. No. 08/132,744 filed Oct. 6, 1993, now U.S. Pat. No. 5,514,822, which is a continuation-in-part of U.S. patent application Ser. No. 993,380 filed Dec. 18, 1992, now U.S. Pat. No. 5,456,945, Ser. No. 07/981,133 filed Nov. 24, 1992, now U.S. Pat. No. 5,423,285, and Ser. No. 07/965,190 filed Oct. 23, 1992, now abandoned; the latter two applications are in turn continuations-in-part of U.S. patent application Ser. No. 07/807,439 filed Dec. 13, 1991, now abandoned.

BACKGROUND OF THE INVENTION

1. Field of the Invention

The invention in general relates to the fabrication of metal oxides utilizing a precursor liquid applied to a substrate, and more particularly to a fabrication process in which the metal-oxygen-metal bonds of the final desired material are largely formed in the precursor liquid prior to the application of the liquid to the substrate.

2. Statement of the Problem

Metal oxides are well known to be useful as ferroelectrics, high dielectric constant materials, and to have many other applications. Recently, there has been much research directed toward using metal oxides in thin film applications, such as integrated circuits. However, their commercial use in such applications has been relatively limited up to the present time. To a significant extent, this is due to the difficulty of forming high quality thin films with precisely controlled composition.

Metal oxide films have perhaps most frequently been formed by sputtering. See for example, Kuniaki Koyama, et al., "A Stacked Capacitor With $(Ba_xSr_{1-x})TiO_3$ For 256M DRAM" in IDEM(International Electron Devices Meeting) Technical Digest December 1991, pp. 32.1.1–32.1.4, and U.S. Pat. No. 5,122,923 issued to Shogo Matsubara et al. Other fabrication methods include pulsed laser deposition, and rapid quenching as listed in Joshi, P. C. et al., "Structural and Optical Properties of Ferroelectric Thin Films By Sol-gel Technique," Appl. Phys. Lett., Vol 59, No. 10, Nov. 91. All of the above methods are relatively violent processes and thus inherently result in relatively poor control of the composition of the final thin film as a whole and variable composition throughout the film. To better control the composition, methods in which a organic liquid precursor is applied to the film and then decomposed to form the metal oxide have been developed. One such method comprises the application of a sol-gel to a substrate followed by heating which decomposes the sol-gel and drives off the organics to form the metal oxide. See for example, U.S. Pat. No. 5,028,455 issued to William D. Miller et al., the Joshi article cited above, and B. M. Melnick, et al., "Process Optimization and Characterization of Device Worthy Sol-Gel Based PZT for Ferroelectric Memories", in Ferroelectrics, Vol 109, pp. 1–23 (1990). In another method, what has been termed a "MOD" solution is applied to a substrate followed by heating which decomposes the MOD solution and drives off the organics to form the metal oxide. See "Synthesis of Metallo-organic Compounds for MOD Powers and Films", G. M. Vest and S. Singaram, Materials Research Society Symposium Proceedings, Vol. 60, 1986 pp. 35–42 and "Metalorganic Deposition (MOD): A Nonvacuum, Spin-on, Liquid-Based, Thin Film Method", J. V. Mantese, A. L. Micheli, A. H. Hamdi, and R. W. Vest, in MRS Bulletin, October 1989, pp. 48–53. In each of these prior art processes, the word "precursor" is used with two different meanings. Each process includes precursors for each individual metal, which precursors we shall call "initial precursors" herein. For example, in the first Vest paper referenced above, barium neodeconate is listed as the initial precursor of choice for the metal barium while bismuth 2-ethylhexanoate is listed as the initial precursor for the metal bismuth. The initial precursors are then dissolved in a common solvent to form a "final precursor" which contains all of the metals of the desired final thin film. Generally the sol-gel method utilizes metal alkoxides as the initial precursors, while the MOD technique utilizes metal carboxylates as the initial precursors. One sol-gel reference, the Miller patent referenced above, mentions one metal carboxylate, lead tetra-ethylhexanoate, as a possible precursor, however does not disclose how this may be used as a sol-gel, and furthermore rejects this precursor as less desirable since the large organic group was thought to result in more defects in the final film. The above liquid precursor methods produce a much better quality film than the previous more violent methods, since the metal and oxygen atoms are relatively uniformly distributed over the substrate. However, in most of the above processes, the metals in the precursor solution are linked by organic ligands, which ligands must be broken down and removed during the heating process. This creates relatively large distances across which the metal and oxygen atoms must link. This often results in cracking or other imperfections in the film, or requires careful control of other parameters, such as film thickness, drying and annealing temperatures, the substrate used etc. In other liquid processes, such as the sol-gel process described in Melnick, the metal-oxygen-metal bonds of the final metal oxide are present in some degree, however the precursor is highly unstable and therefore is difficult to use except immediately after preparation in the laboratory. Thus it would be highly desirable to have a fabrication process in which the constituents can be carefully controlled as in the sol-gel and MOD processes, and at the same time the metal and oxygen atoms are more closely associated prior to the formation of the final desired film and the precursors are sufficiently stable to be used in commercial manufacturing processes.

SUMMARY OF THE INVENTION

The present invention solves the above problem by utilizing a mixed alkoxide/carboxylate initial precursor. Unlike the prior art which utilizes either a metal alkoxide or a metal carboxylate as the individual precursor for a metal, the invention utilizes a alkoxyycarboxylate as the individual precursor for at least one metal.

In an exemplary embodiment or the invention a first metal is reacted with an alcohol and a carboxylic acid to produce a metal alkoxycarboxylate initial precursor. Then the alkoxide of a second metal is added to the alkoxyycarboxylate and reacted to form a final precursor containing both the first and second metals. In this final precursor the first and second metals are linked with a metal-oxygen-metal bond. A portion of the organics that remained in the prior art precursors until after application of the final precursor to the substrate are boiled out of the final precursor as ethers. Generally the organics which remain are alkoxide and carboxylate ligands which are linked to the metal oxide without significantly disturbing the metal-oxygen-metal bonds. The presence of the carboxylate ligands provide sufficient stability to the precursor against hydrolysis to permit it to be stored for months without significantly changing. During and/or after the application of the precursor to a substrate, these remaining organics are disassociated from the metal-oxygen-metal bonds, preferably by heating, thereby leaving the metal-oxygen-metal bonds in place.

In another embodiment a metal carboxylate is combined with a metal alkoxide and heated, preferable with the addition of carboxylic acid and/or alcohol. Many other variations of the process are possible.

The invention provides a method of making a precursor for fabricating a metal oxide, the method comprising the steps of: mixing a metal alkoxycarboxylate-containing liquid with a 2-ethylhexanoic acid in an effective amount for shelf-stabilizing the liquid by substituting 2-ethylhexanoate ligands for alkoxide ligands, thereby forming a mixture; and heating the mixture to so substitute the carboxylate ligands for the alkoxide ligands. Preferably, the method further includes a step of providing the metal alkoxycarboxylate to at least two metals selected from a metal group consisting of barium, strontium, tantalum, calcium, bismuth, lead, yttrium, scandium, lanthanum, antimony, chromium, thallium, titanium, hafnium, tungsten, niobium, zirconium, manganese, iron, cobalt, nickel, magnesium, zinc, and mixtures thereof. Preferably, the metals are provided in effective amounts for forming strontium bismuth tantalate, strontium bismuth niobate, strontium bismuth tantalum nolobate, barium bismuth tantalate, lead bismuth tantalate, or barium bismuth niobate upon drying and calcining of the precursor. Preferably, the precursor has a shelf life exceeding at least two months.

In another aspect, the invention also provides a method of making a barium strontium titanate precursor, the method comprising the steps of: combining a polyoxyalkylated barium moiety, a polyoxyalkylate strontium moiety, and a polyoxyalkylated titanium moiety to form a liquid solution, each of the respective moieties having a formula in which corresponding barium, strontium, and titanium atoms bond with an oxygen atom in a ligand selected from a ligand group consisting of alkoxides and carboxylates; and heating the liquid solution. Preferably, the formula defines a member selected from a moiety group consisting of barium carboxylates, barium alkoxides, barium alkoxycarboxylates, strontium carboxylates, strontium alkoxides, strontium alkoxycarboxylates, titanium carboxylates, titanium alkoxides, and titanium alkoxycarboxylates. Preferably, the heating step includes reacting two members of the moiety group to form a reaction product having a molecular formula including a central oxygen atom connecting two metal atoms, the two members including a single-metal alkoxycarboxylate and a metal alkoxide.

Since a significant portion of the metal-oxygen-metal bonds of the final thin film are already formed in the final precursor, the resulting thin film is of higher quality and less susceptible to cracking and other defects than thin films formed with the prior art processes and precursors. In addition, since the metal and oxygen atoms are much more closely associated in the precursor, the quality of the film is less sensitive to the substrates and/or the process parameters used. Thus the precursors and process of the invention lend themselves more readily to large scale manufacturing. Numerous other features, objects and advantages of the invention will become apparent from the following description when read in conjunction with the accompanying drawings.

BRIEF DESCRIPTION OF THE DRAWINGS

FIG. 4 is a top view of a silicon wafer on which thin film capacitors according to the invention are shown greatly enlarged;

FIG. 5 is a portion of the cross-section of FIG. 4 taken through the lines 5—5, illustrating a thin film capacitor device having buffer layers made with a precursor solution according to the invention;

FIG. 6 is a cross-sectional illustration of a portion of a thin film capacitor made with a precursor solution according to the invention;

DESCRIPTION OF THE PREFERRED EMBODIMENT

1. Overview

Figure 1:
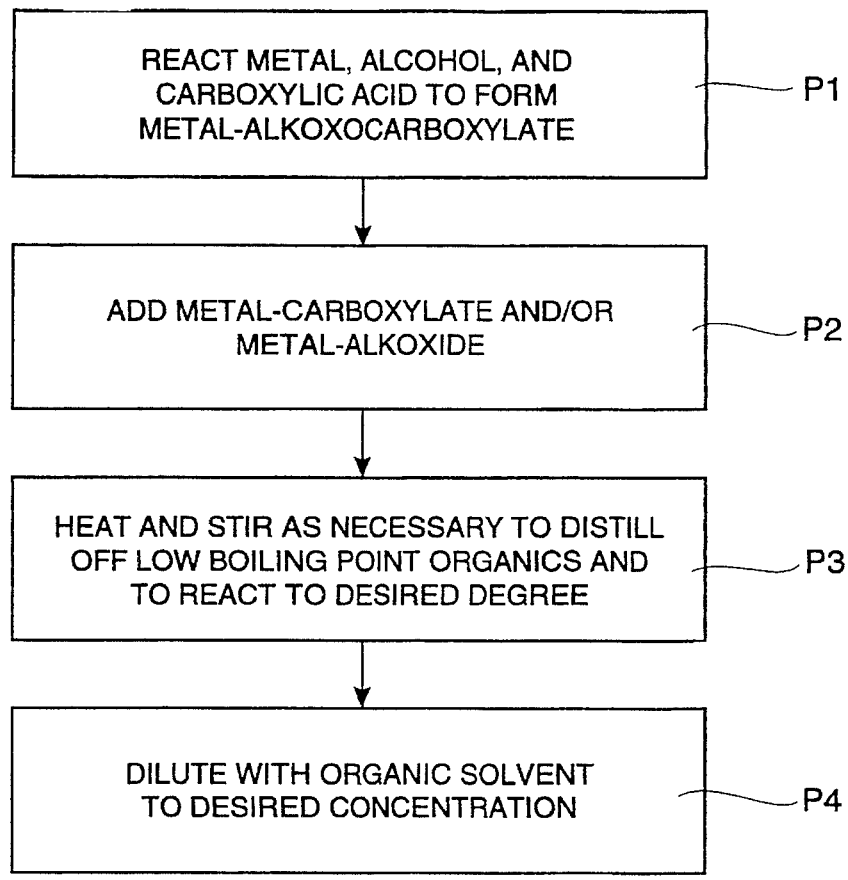
FIG. 1 is a flow chart showing the preferred embodiment of a process for preparing a precursor solution according to the invention.

Directing attention to FIG. 1, there is shown a flow chart of a generalized process according to the invention for forming a precursor solution for fabricating thin films. As indicated above, the word "precursor" is often used ambiguously in this art. It may mean an solution containing one metal or the a solution containing several metals which is applied to a substrate. In this discussion we shall generally refer to the individual precursors as "initial precursors" and the precursor as applied to the substrate as the "final precursor" or just "precursor" unless the meaning is clear from the context. In intermediate stages the solution may be referred to as the "intermediate precursor". In step P1 a 1st metal, indicated by the term metal (1), is reacted with an alcohol and a carboxylic acid to form a metal-alkoxocarboxylate initial precursor. A metal-alkoxocarboxylate is a compound of the form $MX_xA_a$, where M is a metal, X is a carboxylate ligand and A is an alkoxide ligand. The subscripts indicate the number of units of the ligand required to agree with the valence requirements. Metals that may be used include barium, strontium, tantalum, calcium, bismuth, lead, yttrium, scandium, lanthanum, antimony, chromium, thallium, titanium, hafnium, tungsten, niobium, zirconium, manganese, iron, cobalt, nickel, magnesium, zinc, and other elements. Alcohols that may be used include 2-methoxy-ethanol, 1-butanol, 1-pentanol, 2-pentanol, 1-hexanol, 2-hexanol, 3-hexanol, 2-ethyl-1-butanol, 2-ethoxyethanol, and 2-methyl-1-pentanol, preferably 2-methoxyethanol. Carboxylic acids that may be used include 2-ethylhexanoic acid, octanoic acid, and neodecanoic acid, preferably 2-ethylhexanoic acid. In a typical second step, P2, a metal-carboxylate, a metal-alkoxide or both may be added to the metal-alkoxocarboxylate. Any of the metals listed above reacted with any of the carboxylic acids listed above may form the carboxylate, while any of the metals listed above reacted with any of the alcohols may form the alkoxide. In step P3 the mixture of metal-alkoxocarboxylate, metal-carboxylate and/or metal-alkoxide is heated and stirred as necessary to form metal-oxygen-metal bonds and boil off any low-boiling point organics that are produced by the reaction. Preferably, at least 50% of the metal-oxygen-metal bonds of the final desired metal oxide are formed by the end of this step. In step P4 the solution is diluted with an organic solvent to produce the final precursor of the desired concentration. A solvent exchange step may take place simultaneously or subsequently to change the solvent. Solvents that may be used include: xylenes, 2-methoxyethanol, n-butyl acetate, n-dimethylformamide, 2-methoxyethyl acetate, methyl isobutyl ketone, methyl isoamyl ketone, isoamyl alcohol, cyclohexanone, 2-ethoxyethanol, 2-methoxyethyl ether, methyl butyl ketone, hexyl alcohol, 2-pentanol, ethyl butyrate, nitroethane, pyrimidine, 1, 3, 5 trioxane, isobutyl isobutyrate, isobutyl propionate, propyl propionate, ethyl lactate, n-butanol, n-pentanol, 3-pentanol, toluene, ethylbenzene as well as many others.

If a metal-alkoxide is added to the metal-alkoxocarboxylate and the solution is heated the following reactions occur:

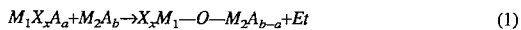

$$M_1X_xA_a+M_2A_b \rightarrow X_xM_1\text{—}O\text{—}M_2A_{b-a}+Et \quad (1)$$

and

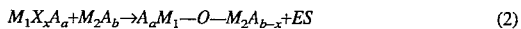

$$M_1X_xA_a+M_2A_b \rightarrow A_aM_1\text{—}O\text{—}M_2A_{b-x}+ES \quad (2)$$

where $M_1$ is the first metal, $M_2$ is the second metal, X and A and the subscripts are as defined above, O is oxygen, Et is an ether, and Es is an ester. The dashes indicate metal-oxygen-metal bonds. Generally the reaction of equation (1) will occur first since alkoxides react more readily than carboxylates. Thus ethers, which have low boiling points are generally formed. These ethers boil out of the precursor, thus leaving a reduced organic final precursor with the metal-oxygen-metal bonds of the final desired metal oxide already partially formed. If the heating is sufficient, some of the reaction (2) will also occur, creating metal-oxygen-metal bonds and esters. Esters generally have higher boiling points and remain in solution. Such high boiling point organics slow down the drying process after the final precursor is applied to a substrate, which tends to reduce cracking and defects. Thus, in either case metal-oxygen-metal bonds are formed and the final precursor performance is improved.

If a metal-carboxylate is added to the metal-alkoxocarboxylate and the mixture is heated, the following reaction occurs:

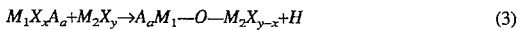

$$M_1X_xA_a+M_2X_y \rightarrow A_aM_1\text{—}O\text{—}M_2X_{y-x}+H \quad (3)$$

where H is a carboxylic acid anhydride. This reaction requires considerably more heat than the reactions (1) and (2) above, and proceeds at a much slower rate.

The above reaction summary is generalized and the specific reactions that occur depend on the metals, alkoxides, and carboxylates used, as well as the amount of heat that is applied. Detailed examples will be given below.

Figure 2:
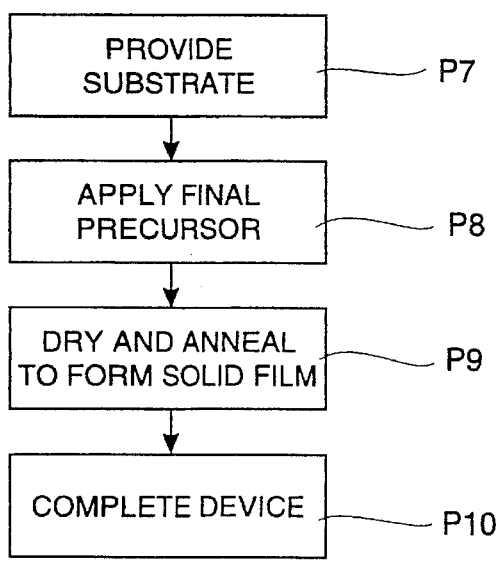
FIG. 2 is a flow chart showing the application of a precursor solution according to the invention to produce a solid thin film which is incorporated into an electronic device.
Figure 7:
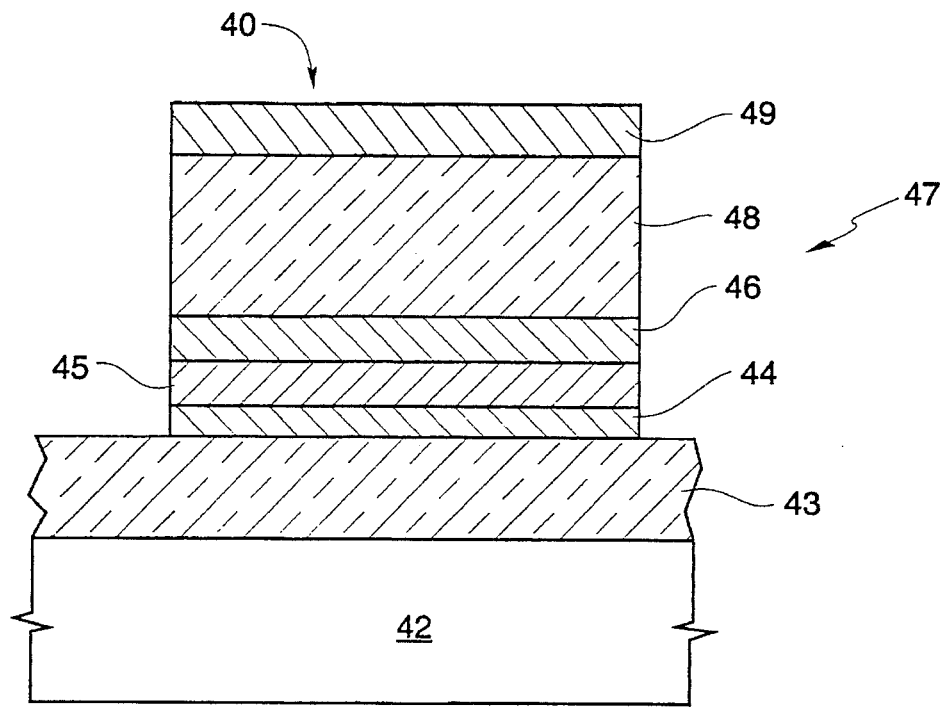
FIG. 7 is a cross-sectional illustration of a portion of another embodiment of a thin film capacitor made with a precursor solution according to the invention.
Figure 8:
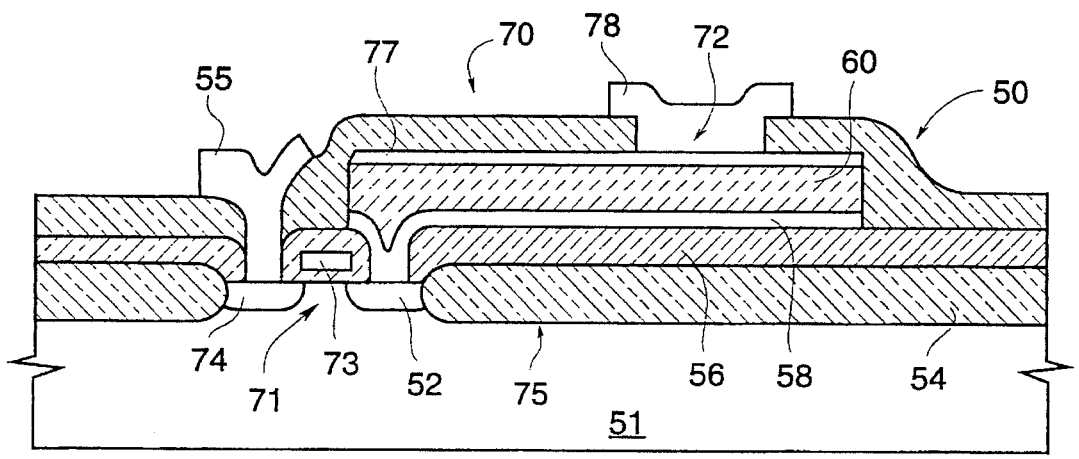
FIG. 8 is a cross-sectional view of an individual integrated circuit memory cell as may be fabricated using a precursor according to the invention.

In FIG. 2, a flow chart showing, also in generalized form, the application of the final precursor according to the invention to form a thin film. In step P7 a substrate is provided. The substrate generally would be an incomplete integrated circuit, or other electrical device. Examples are shown in FIGS. 4 through 8. It should be understood that the FIGS. 4 through 7 depicting capacitor devices and FIG. 8 depicting an integrated circuit device are not meant to be actual plan or cross-sectional views of any particular portion of an actual capacitor or integrated circuit device, but are merely idealized representations which are employed to more clearly and fully depict the structure and process of the invention than would otherwise be possible. FIG. 5 shows a cross-section of the wafer 1 of FIG. 2A taken through the line 5—5. FIGS. 6 and 7 depict a cross-section taken through a wafer similar to that of FIG. 4 but having a different layered structure. Referring to FIGS. 4 and 5, the wafer 1 preferably comprises a P-type silicon substrate 2 on which an approximately 5000 Å silicon dioxide insulating layer 4 has been wet grown. A thin layer 6 of titanium metal has been deposited on the silicon dioxide 4, preferably by sputtering in situ, and a 2000 Å thick electrode of platinum has been deposited on the titanium 6, preferably by sputtering in situ. By "in situ" is meant that both the titanium and the platinum are sputtered without breaking vacuum. The titanium diffuses into the silicon dioxide and platinum and assists the platinum 8 in adhering to the silicon dioxide 4, and is optional. In the preferred embodiment, the layer 6 may also include a barrier layer of, for example, TiN. The barrier layer prevents ion migration between the silicon of layer 4 and the electrode 8 and layers 10 and 12. The structure of such adhesion layers, barrier layers, and electrodes are well know in the art and will not be discussed in detail herein. A buffer layer 10, is deposited on the platinum electrode 8, followed by a layer 12 of metal oxide according to the invention, followed by another buffer layer 14, via processes that will be described in detail in the examples below. Another 2000 Å layer of platinum is deposited on the buffer layer 14. The wafer 1 is annealed, patterned with a photo-mask process, and etched down to the electrode layer 8 to produce rectangular capacitor devices 17A, 17B, etc. (FIG. 4) of various sizes separated by large areas of the electrode 8. In the annealing process, the materials of layers 10 and 14 may interdiffuse with the materials of layer 12 forming interface layers 11 and 15, respectively. The size of the devices 17A, 17B, etc. is greatly exaggerated in FIG. 4. Each device 17A, 17B, etc. may be tested by connecting one lead of the test device to the platinum electrode layer 8 and contacting the other electrode layer 16 of the particular device 17A, 17B, etc. with a fine probe connected to the other lead of the test device. Devices having the cross-sectional structure of FIG. 6 are similarly fabricated except that the two buffer layers 10, 12 are not deposited. That is, the wafer of FIG. 6 includes a silicon substrate 22, a silicon dioxide layer 24, an optional titanium layer 26, a first platinum electrode 28, a metal oxide layer 30, and a second platinum electrode 32. The wafer 20 is similarly patterned to form capacitor devices of various sizes having the cross-section shown in FIG. 6. The capacitor 40 of FIG. 7 includes a silicon substrate 42, a silicon dioxide insulating layer 43, a titanium adhesion layer 44, a titanium nitride barrier layer 45, a platinum first electrode 45, a layer of metal oxide 48, and a platinum second electrode 49. The fabrication of exemplary devices of the types shown in FIGS. 4 through 7 will be described in detail in the examples below.

FIG. 8 shows an example of the integration of a thin film metal oxide 60 according to the invention into a DRAM memory cell 50 to form an integrated circuit 70 such as may be fabricated using the invention. The memory cell 50 includes a silicon substrate 51, field oxide areas 54, and two electrically interconnected electrical devices: a transistor 71 and a capacitor 72. Transistor 71 includes a gate 73, a source 74, and a drain 52. Capacitor 72 includes first electrode 58, metal oxide thin film 60, and second electrode 77. Capacitor 72 may either be a ferroelectric switching capacitor, in which case metal oxide 60 would be a ferroelectric, or a normal capacitor, in which case metal oxide 60 would be a dielectric and may or may not be ferroelectric. Insulators, such as 56, separate the devices 71, 72, except where drain 52 of transistor 71 is connected to first electrode 58 of capacitor 72. Electrical contacts, such as 55 and 78 make electrical connection to the devices 71, 72 to other parts of the integrated circuit 70. Electrode 58 will as well as the other conducting layers will generally be multilayered conductors including adhesion and barrier layers as is well-known in the art.

From the above it can be seen that in the case of the wafer 1 of FIG. 5, when considering the deposition of buffer layer 10, the substrate 18 referred to in step P7 (FIG. 2) comprises layers 2, 4, 6, and 8. In the case of the deposition of layer 30 of wafer 20 of FIG. 6, the substrate 38 comprises layers 22, 24, 26, and 28. And in the case of the integrated circuit 70 of FIG. 7, the substrate 75 comprises layers 51, 54, 56, and 58. Returning to FIG. 2, the final precursor liquid is applied to the substrate 18, 38, 75. The application may be by a misted deposition process as described in U.S. patent application Ser. No. 993,380, though other methods of applying a liquid to a substrate may be used. The precursor on the substrate is then treated, to form a solid metal oxide thin film. Generally it is treated by heating, but as described in U.S. patent application Ser. No. 993,380, it may also be by exposing the substrate and precursor to a vacuum. In the preferred embodiment, the precursor is treated by drying and annealing. Then the device 1, 20, 70 is completed. The steps P7 through P10 are generally known in the art, and thus will not be discussed in detail here, although some examples will be given below.

A term that is used frequently in this disclosure is "stoichiometry" or "stoichiometric". As used herein, the term stoichiometric generally expresses a relationship between the final precursor solution and the desired metal oxide film 30. A "stoichiometric precursor" is one in which the relative proportions of the various metals in the precursor is the same as the proportion in a homogeneous specimen of the intended metal oxide thin film 30. This proportion is the one specified by the formula for the metal oxide thin film 30. When we say that the process permits one to better control the stoichiometry, we mean that the process permits one to better control the proportion of the various elements in the metal oxide film 30.

2. Detailed Description of Exemplary Embodiments

Turning now to a more detailed description of the invention, examples of precursors according to the invention and processes according to the invention for utilizing the precursors are given below. All processes were performed at the atmospheric pressure in Colorado Springs, Colorado, except where otherwise noted. An exemplary flow chart illustrating the process according to the invention for preparing the first precursor example, a final precursor for fabricating a barium strontium titanate (BST) thin film, is shown in FIG. 3.

EXAMPLE 1

Barium Strontium Titanate (BST) —$Ba_{0.7}Sr_{0.3}TiO_3$

Figure 3:
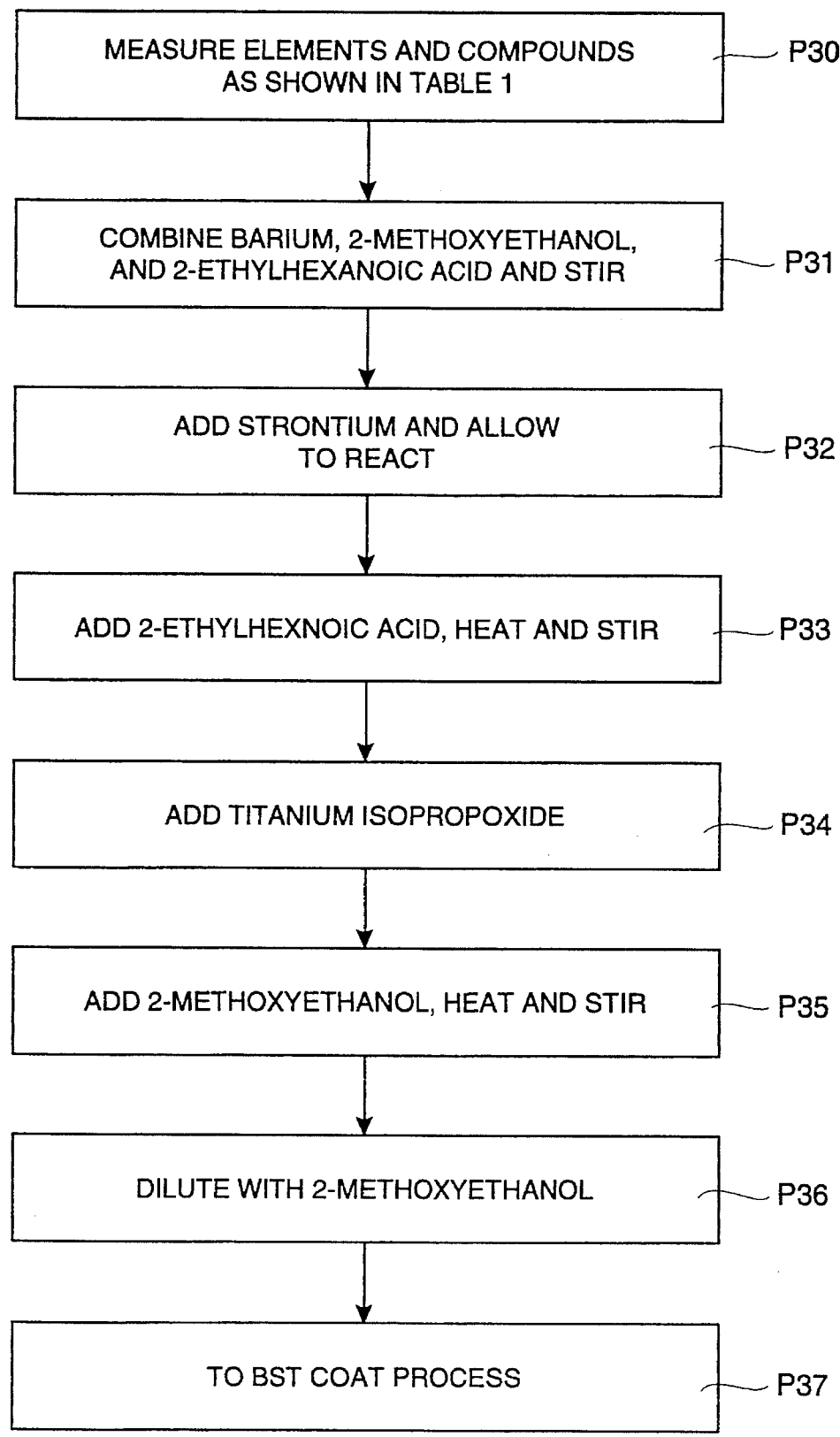
FIG. 3 is a flow chart showing an exemplary embodiment of the process of the invention to produce a precursor for BST.

Referring to FIG. 3, in step P30 the compounds shown in Table I were measured.

TABLE I

| Compound | FW | g | mmole | Equiv. |
|---|---|---|---|---|
| Barium | 137.327 | 9.4255 | 68.635 | 0.69986 |
| 2-ethylhexanoic acid | 144.21 | 19.831 | 137.51 | 1.4022 |
| Strontium | 87.62 | 2.5790 | 29.434 | 0.30014 |
| 2-ethylhexanoic acid | 1.44.21 | 8.5005 | 88.945 | 0.6010 |
| Titanium Isopropoxide | 284.26 | 27.878 | 98.072 | 1.0000 |

In the above table and the tables below, "FW" indicates formula weight, "g" indicates grams, "mmoles" indicates millimoles, and "Equiv." indicates the equivalent number of moles in solution. In the preferred embodiment of step P31 the barium is placed in 100 ml (milliliters) of 2-methoxyethanol, the 2-ethylhexanoic acid is added and the mixture is allowed to react while stirring. The step may also be preformed by placing the barium in the 2-methoxyethanol, allowing it to react, adding the 2-ethylhexanoic acid, and stirring while it reacts. In either case the reaction may be described by the following equation:

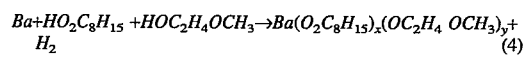
$$Ba + HO_2C_8H_{15} + HOC_2H_4OCH_3 \rightarrow Ba(O_2C_8H_{15})_x(OC_2H_4 OCH_3)_y + H_2 \qquad (4)$$

where $HO_2C_8H_{15}$ is 2-ethylhexanoic acid, $HOC_2H_4OCH_3$ is 2-methoxyethanol, $(O_2C_8H_{15})$ is the carboxylate ligand, $(OC_2H_4OCH_3)$ is the alkoxide ligand, and x and y indicate the number of each ligand that is bonded to the barium. Usually, both x and y are approximately 1. $H_2$, hydrogen gas, is a by-product of the reaction and escapes from the solution. The reaction of the barium heats the solution. While the solution is still hot, the strontium is added in step P32 and allowed to react. The heat in solution from the barium reaction assists the strontium reaction. When the strontium is all reacted, then, in step P33, the second measure of 2-ethylhexanoic acid is added and, while stirring, the solution is heated to a maximum temperature of 115° C. This ensures that any water present is distilled out. This is believed to result in a similar reaction to that of equation (4) except that Sr replaces Ba.

In addition to the above reactions which produce metal-alkoxocarboxylates, reactions such as:

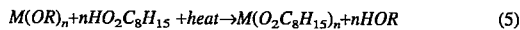
$$M(OR)_n + nHO_2C_8H_{15} + heat \rightarrow M(O_2C_8H_{15})_n + nHOR \qquad (5)$$

where M is a metal, R is the alkyl group, n is an integer, $M(OR)_n$ is the alkoxide, $HO_2C_8H_{15}$ is 2-ethylhexanoic acid, $M(O_2C_8H_{15})_n$ is a metal 2-ethylhexanoate, and HOR is an alcohol, which reactions completely transform the alkoxide part of the intermediate metal-alkoxocarboxylate to full carboxylates, also occur. However, it is believed that the complete substitution of the alkoxides by the carboxylates, as previously thought, does not occur with the parameters as disclosed herein. Full substitution of the carboxylates requires significantly more heating, and even then may not readily occur.

The mixture is then allowed to cool, and in step P34 the titanium isopropoxide is added followed by the addition of enough 2-methoxyethanol in step P35 to make 220 ml total solution. The solution is then heated and stirred with the following reactions:

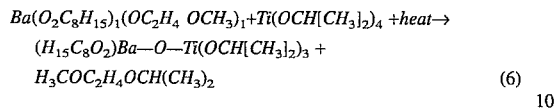

and

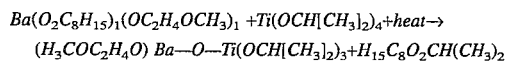

where Ti(OCH[CH$_3$]$_2$)$_4$ is titanium isopropoxide, H$_3$COC$_2$H$_4$OCH(CH$_3$)$_2$ is 2-methoxy-ethoxy-isopropyl ether, and H$_{15}$C$_8$O$_2$CH(CH$_3$)$_2$ is isopropyl 2-ethylhexanoate, an ester. Similar reactions occur for the strontium.

The ethers and some esters can be smelled during this reaction. The ethers are low boiling point liquids and generally boil out of solution while the esters are higher boiling point liquids which tend to remain in solution. During the heating, the maximum temperature is 116° C. which also ensures that all isopropanol and water will be boiled out. The solution is then diluted to 200 ml total solution with additional 2-methoxyethanol in step 36. The result is a final BST precursor of 0.490 Moles concentration with the ratio of barium to strontium equal to 0.69986:0.30014.

The BST precursor solution made above was utilized to fabricate a capacitor as shown in FIG. 7. The capacitor was fabricated by forming the silicon dioxide 43 by thermal oxidation in a furnace, followed by sputter deposition of the titanium, titanium nitride, and platinum layers 44, 45, and 46 respectively, to form the substrate 47. The BST precursor solution was then utilized to apply a layer 48 of BST of about 140 nm (nanometers) thick in the BST coat process P37. The BST was annealed in an oxygen furnace at 750° C. Then electrode 49 was deposited by sputtering. Further details of the deposition process may be found in Copending U.S. patent application Ser. No. (2008/02). The dielectric constant of the BST film 48 was measured to be about 490, the leakage current of the capacitor 40 was approximately 2×10$^{-9}$ Amps/cm$^2$ under a voltage of approximately 3.3 volts, and a TDDB characteristic curve showed the life time to breakdown to be over 100 years under a stress of 5 volts. The grain size of the BST layer 48 was about 40 nm. These results indicate that the precursor and process of making the precursor may be used to yield BST thin films of much higher quality than in the prior art. The size of the dielectric constant, the low leakage current at voltages used in state-of-the-art integrated circuits, and the TDDB characteristics all indicate that a BST film 60 (FIG. 8) should have superior performance in an integrated circuit, such as that shown in FIG. 8.

EXAMPLE 2

Bismuth Titanate Between Buffer Layers of Strontium

Titanate —SrTiO$_3$/Bi$_4$Ti$_3$O$_{12}$/SrTiO$_3$

The compounds shown in Table II were measured.

TABLE II

| Compound | FW | g | mmole | Equiv. |
| --- | --- | --- | --- | --- |
| Bismuth 2-ethylhexanoate | (638.61) | 21.2578 | 24.6328 | 4.00000 |
| Titanium Isopropoxide | 284.26 | 5.2517 | 18.4750 | 3.00006 |
| Strontium | 87.62 | 2.8023 | 31.982 | 1.0000 |
| 2-ethylhex-anoic acid | 144.21 | 9.2283 | 63.992 | 2.0009 |
| Titanium Isopropoxide | 284.26 | 9.0912 | 31.982 | 1.0000 |

In the above table and the tables below, bismuth 2-ethylhexanoate indicates a commercially available bismuth solution of bismuth 2-ethylhexanoate in 74% naphtha; the formula weight in this case is placed in parenthesis to indicate that it is an equivalent formula weight of bismuth in the solution as a whole, rather than the formula weight of the just the bismuth 2-ethylhexanoate, in order to take into account the presence of the naphtha. The bismuth 2-ethylhexanoate was placed in 0 ml xylenes. Here and where used below, "xylenes" indicates a commercially available xylene solution which includes the three different isomers of xylene. The solution was stirred and heated to a maximum temperature of 117° C. to distill out all light hydrocarbon fractions and water. The first measure of titanium isopropoxide was combined with 60 ml of 2-methoxyethanol, and was stirred and heated to a maximum temperature of 116° C. to distill out all water and isopropanol. The bismuth solution and the titanium solution were combined, then heated to a maximum temperature of 136° C. to distill out all 2-methoxyethanol and some xylenes until 60 ml of solution remained. The concentration was 0.1206 moles of Bi$_4$Ti$_3$O$_{12}$ per liter with 0.002% excess titanium.

The strontium was placed in the 2-ethylhexanoic acid together with 50 ml 2-methoxyethanol. The solution was stirred and heated to a maximum temperature of 115° C. to distill off all light hydrocarbon fractions and water and to produce a strontium-alkoxocarboxylate as discussed above. Also, as discussed above, the strontium could be reacted with the 2-methoxyethanol first and then add the 2-ethylhexanoic acid after the initial reaction has taken place. The second measure of titanium isopropoxide was dissolved in 50 ml methoxyethanol and stirred and heated to a maximum of 115° C. to distill off the isopropanol and water. The strontium and titanium solutions were combined and stirred and heated to a maximum temperature of 125° C. to distill down to a volume of 60.0 ml. This created a mixture of XSr—O—TiA and ASr—O—TiA structures as discussed above as well as some full carboxylates. The concentration was 0.533 moles of SrTiO$_3$ per liter. Just prior to use, a xylene exchange was performed by adding 25 ml of xylenes to 5 ml of the above SrTiO$_3$ solution and stirred and heated to a maximum temperature of 128° C. to distill out 7 ml to produce a final solution of 23 ml (milliliter) volume and a concentration of 0.116 moles of SrTiO$_3$ per liter.

A substrate 18 (FIG. 5) was baked at 140° C. in air for 30 minutes to dehydrate it. An eyedropper was used to place 1 ml of the $SrTiO_3$ solution on the substrate 18, which was then spun at 1500 RPM for 20 seconds. The wafer 1 was then placed on a hot plate and baked at 50° C. in air for four minutes. An eyedropper was used to place 1 ml of the $Bi_4Ti_3O_{12}$ solution on the wafer and the wafer was spun at 1500 RPM for 20 seconds. The wafer was placed on a hot plate and baked at 250° C. for 4 minutes. The steps from using an eyedropper to deposit 1 ml of $SrTiO_3$ solution on the wafer through baking on the hot plate were repeated for another $SrTiO_3$ layer 14. The wafer was then transferred to a diffusion furnace and annealed at 700° C. in an oxygen flow of 5 l/m (liters/minute) for 50 minutes. The top layer 16 of 2000 Å platinum was sputtered, a resist was applied, followed by a standard photo mask process, an ion mill etch, an IPC strip and a final contact anneal at 700° C. in an oxygen flow of 5 l/m for 50 minutes. Hysteresis and switching fatigue tests, as described in U.S. patent application Ser. No. 07/981,133, were performed on the sample, and the results indicated that at the interface of the layers 10 and 14 and the layer 12 thin layers of strontium bismuth titanate 11 and 15 was formed, which strontium bismuth titanate exhibited very low fatigue, having a polarizability that remained almost unchanged all the way out past $10^9$ cycles.

EXAMPLE 3

Strontium Bismuth Tantalate —$SrBi_2Ta_2O_9$

The compounds shown in Table III were measured. The strontium was combined with the first measure of 2-ethylhexanoic acid and 80 ml 2-methoxyethanol. The mixture was stirred on low heat of between about 70° C. and 90° C. to hurry the reaction rate. When all the strontium was

TABLE III

| Compound | FW | g | mmole | Equiv. |
|---|---|---|---|---|
| Tantalum ethoxide | 406.26 | 4.9553 | 12.197 | 2.0000 |
| 2-ethylhexanoic acid | 144.21 | 8.7995 | 61.019 | 10.006 |
| Strontium | 87.62 | 0.5330 | 6.0831 | 0.9975 |
| 2-ethylhexanoic acid | 144.21 | 1.7613 | 12.213 | 2.0026 |
| Bismuth 2-ethylhexanoate | (862.99) | 10.525 | 12.196 | 1.9998 | reacted and the solution had cooled to approximately room temperature, the tantalum ethoxide followed by the second measure of 2-ethylhexanoic acid were added. The mixture was stirred and heated to a maximum temperature of 115° C. Then 75 ml xylenes followed by the bismuth 2-ethylhexanoate were added. The solution was stirred and heated with a maximum temperature of about 125° C. until only 60.0 ml of solution remained. The concentration was 0.102 moles of $SrBi_2Ta_2O_9$ per liter. A substrate 38 (FIG. 6) was baked at 140° C. in air for 30 minutes to dehydrate it. An eyedropper was used to place 1 ml of the $SrBi_2Ta_2O_9$ solution on the substrate 38, which was then spun at 1500 RPM for 20 seconds. The wafer 1 was then placed on a hot plate and baked at above 250° C. in air for three minutes. The steps from using an eyedropper to deposit solution on the wafer through baking on the hot plate were repeated for another layer. The wafer was then transferred to a diffusion furnace and annealed at 750° C. in an oxygen flow of 5 liters/minute for 2 hours. The top layer 32 of 2000 Å platinum was sputtered, a resist was applied, followed by a standard photo mask process, an ion mill etch, an IPC strip and a final contact anneal at 750° C. in an oxygen flow of 5 l/m for 30 minutes. The resulting sample was tested via hysteresis curves and demonstrated almost no fatigue over $10^{10}$ cycles. Moreover the hysteresis curves were very boxy and vertical, yielding large polarizability. These results are phenomenal when compared to the prior art materials, and indicate that the precursors and process of the invention should yield excellent integrated circuits.

EXAMPLE 4

Strontium Bismuth Niobate —$SrBi_2Nb_2O_9$

The compounds shown in Table IV were measured.

TABLE IV

| Compound | FW | g | mmole | Equiv. |
|---|---|---|---|---|
| strontium | 87.62 | 0.5625 | 6.4198 | 1.0000 |
| 2-ethylhexanoic acid | 144.21 | 2.0940 | 14.520 | 2.2618 |
| bismuth 2-ethylhexanoate | (862.99) | 11.079 | 12.838 | 1.9998 |
| niobium butoxide | 458.48 | 5.8862 | 12.839 | 1.9999 |
| 2-ethylhexanoic acid | 144.21 | 9.2911 | 64.428 | 10.036 |

The strontium was placed in 30 ml 2-methoxyethanol. The first measure of 2-ethylhexanoic acid was added and was allowed to react completely. The bismuth 2-ethylhexanoate was added, followed by 35 ml xylenes. The niobium butoxide and second measure of 2-ethylhexanoic acid was added, followed by 40 ml of xylenes. The mixture was heated and stirred, with a maximum temperature of 123° C., until all the butanol, water, and 2-methoxyethanol were removed. The final volume was 63 ml, and the final mass was 57.475 g. The concentration was 0.102 moles of $SrBi_2Nb_2O_9$ per liter, or 0.1117 mmoles of $SrBi_2Nb_2O_9$ per gram of solution. A capacitor 20 as shown in FIG. 6 was fabricated utilizing this precursor for the layer 30 in a process similar to that of Example 3. The sample was tested and again showed low fatigue and excellent polarizability.

EXAMPLE 5

Strontium Bismuth Tantalum Niobate —$SrBi_2TaNbO_9$

The compounds shown in Table V were measured.

TABLE V

| Compound | FW | g | mmole | Equiv. |
|---|---|---|---|---|
| strontium | 87.62 | 0.5821 | 6.6435 | 1.0001 |
| 2-ethylhexanoic acid | 144.21 | 1.9770 | 13.709 | 2.0635 |
| bismuth 2-ethylhexanoate | (862.99) | 11.4687 | 13.289 | 2.0005 |
| tantalum butoxide | 546.522 | 3.6303 | 6.6426 | 1.0000 |
| niobium butoxide | 458.48 | 3.0456 | 6.6428 | 1.0000 |
| ethylhexanoic acid | 144.21 | 9.6081 | 66.626 | 10.030 |

The strontium was placed in 30 ml of 2-methoxyethanol and the first measure of 2-ethylhexanoic acid was added and allowed to react completely. Then the bismuth 2-ethylhexanoate was added followed by 40 ml xylenes. The tantalum butoxide and the niobium butoxide were added, followed by the second portion of the 2-ethylhexanoic acid and 40 ml additional xylenes. The mixture was stirred and heated to a maximum temperature of 122° C. until 65 ml of solution remained. The concentration was 0.102 moles of $SrBi_2TaNbO_9$ per liter. A capacitor 20 as shown in FIG. 6 was fabricated in a process similar to that described in Example 3 utilizing the precursor to produce a $SrBi_2TaNbO_9$ film 30. The resulting sample was tested and showed a little more fatigue than the samples of Examples 3 and 4 above, but still only about 5% fatigue over $10^9$ cycles, which is ten times better than even the best materials in the prior art. The results show that $SrBi_2TaNbO_9$ made by the process according to the invention should provide non-volatile ferroelectric memory cells 70 (FIG. 8) that last indefinitely.

EXAMPLE 6

Barium Bismuth Tantalate —$BaBi_2Ta_2O_9$

The compounds shown in Table VI were measured.

TABLE VI

| Compound | FW | g | mmole | Equiv. |
|---|---|---|---|---|
| barium | 137.327 | 0.9323 | 6.7889 | 1.0000 |
| 2-ethylhexanoic acid | 144.21 | 1.9733 | 13.684 | 2.0156 |
| bismuth 2-ethylhexanoate | (862.99) | 11.717 | 13.577 | 1.9999 |
| tantalum butoxide | 546.522 | 7.4211 | 13.579 | 2.0002 |
| 2-ethylhexanoic acid | 144.21 | 9.9216 | 68.800 | 10.134 |

The barium was placed in 40 ml of 2-methoxyethanol and 20 ml of toluene, to slow the reaction, and the first measure of 2-ethylhexanoic acid were added and allowed to react completely. Then the bismuth 2-ethylhexanoate was added followed by 40 ml xylenes. The solution was stirred and heated to a maximum temperature of about 123° C. The solution was allowed to cool to room temperature, then the tantalum butoxide was added, followed by the second portion of the 2-ethylhexanoic acid and 40 ml additional xylenes. The mixture was heated to a temperature of about 123° C. while stirring until 66 ml of solution remained. The concentration was 0.103 moles of $BaBi_2Ta_2O_9$ per liter. A capacitor 20 as shown in FIG. 6 was fabricated in a process similar to that described in Example 3 utilizing the precursor to produce a $BaBi_2Ta_2O_9$ thin film 30. The $BaBi_2Ta_2O_9$ was not a switching ferroelectric, but was a paraelectric with a dielectric constant of 166 at 1 megahertz. This is a very high dielectric constant as compared to the dielectric constant of 3.9 for silicon dioxide, the most commonly used dielectric in integrated circuits. The leakage current was negligible, of the order of $10^{-8}$ amps/cm2 over the range of voltages uses in conventional integrated circuits, i.e. 1–10 volts. The thickness of this sample was about the same thickness generally used for dielectrics in conventional integrated circuits. These results show that this material will be an excellent high dielectric material in integrated circuits.

EXAMPLE 7

Lead Bismuth Tantalate —$PbBi_2Ta_2O_9$

The compounds shown in Table VII were measured.

TABLE VII

| Compound | FW | g | mmole | Equiv. |
|---|---|---|---|---|
| Lead 2-ethylhexanoate in xylenes | (1263.6) | 16.691 | 13.209 | 1.1000 |
| bismuth 2-ethylhexanoate | (753.35) | 18.095 | 24.019 | 2.0002 |
| tantalum butoxide | 546.52 | 13.126 | 24.017 | 2.0001 |
| 2-ethylhexanoic acid | 144.21 | 17.967 | 124.59 | 10.375 |

The lead 2-ethylhexanoate in xylenes previously prepared stock solution and the bismuth 2-ethylhexanoate were combined, followed by 40 ml xylenes. Then the tantalum butoxide was added, followed by the 2-ethylhexanoic acid. The mixture was stirred on low heat of between about 70° C. and 90° C. for four hours, then raised to a maximum temperature of 114° C. until 66 ml of solution remained. The concentration was 0.172 moles of $PbBi_2Ta_2O9$ per liter with 10% excess lead. A capacitor 20 as shown in FIG. 6 was fabricated in a process similar to that described in Example 3 utilizing the precursor to produce a thin film 30. The sample was tested and proved to have a dielectric constant of 114 at 1 megahertz and small leakage current.

EXAMPLE 8

Barium Bismuth Niobate —$BaBi_2Nb_2O_9$

The compounds shown in Table VIII were measured.

TABLE VIII

| Compound | FW | g | mmole | Equiv. |
|---|---|---|---|---|
| barium | 137.327 | 0.9419 | 6.8588 | 1.0000 |
| 2-ethylhexanoic acid | 144.21 | 2.0538 | | |
| bismuth 2-ethylhexanoate | (862.99) | 11.838 | 13.717 | 1.9999 |
| niobium butoxide | 458.48 | 6.2894 | 13.718 | 2.0001 |
| 2-ethylhexanoic acid | 144.21 | 10.051 | 69.697 | 10.162 |

The barium was placed in 30 ml of 2-methoxyethanol and 20 ml of toluene, to slow the reaction, and the first measure of 2-ethylhexanoic acid was added and allowed to react completely while stirring. Then the bismuth 2-ethylhexanoate was added followed by 50 ml xylenes. The mixture was stirred and heated with a maximum temperature of 118° C. The solution was allowed to cool to room temperature, then the niobium butoxide was added, followed by the second portion of the 2-ethylhexanoic acid and 30 ml additional xylenes. The mixture was heated to a temperature of 124° C. while stirring until 68 ml of solution remained. The concentration was 0.101 moles of $BaBi_2Nb_2O_9$ per liter. A capacitor 20 as shown in FIG. 6 was fabricated in a process similar to that described in Example 3, utilizing the precursor to produce a thin film 30. The sample was tested and proved to have a dielectric constant of 103.46 and good leakage current results.

In the discussions below, we shall use barium titanate, BaTiO$_3$ and barium strontium titanate, BaSrTiO$_3$, as an exemplary metal oxides. However, it should be understood that the discussion could also be made in terms of other metal oxides. The most commonly used liquid organic method of fabricating metal oxides prior to this invention was the sol-gel process. In the sol-gel process for barium titanate, barium and titanium alkoxides are mixed in organic solvents to form precursors. Barium may also may also be reacted with titanium alkoxide dissolved in alcohol. Despite the fact that such precursors are not stable enough for commercial manufacturing processes, the present inventors and their colleagues have studied them extensively and some of the results are of general importance.

In contrast to the general view that a bi-metallic oxide, such as BaTi(OR)$_6$ where R is the isopropyl radical i-Pr, is the precursor of the oxide phase in solution, we have discovered that the above-mentioned complex does not exist in the sol-gel precursor solutions. It is the oxoalkoxides, such as BaTiO$_x$(OR)$_{6-2x}$, which are formed in the solutions and are the true precursors for the complex oxide BaTiO$_3$. The chemical reactions which lead to the formation of these oxoalkoxides are numerous. We have isolated a series of such complexes in the form of single crystals and solved their structures. For example, one such crystal had the structure BaTiO(OPr—i)$_4$·i—PrOH. In such a structure a Ba—O—Ti core already exists which is preserved in all stages of preparation of BaTiO$_3$ from this precursor. It is noteworthy that the higher the x value the better are the conditions for formation of BaTiO$_3$.

On the other hand, for commercial or other out-of-the-laboratory applications, it is more convenient to use carboxylates as precursors since they are far more stable to hydrolysis, therefore the properties of the prepared solutions do not change over time in storage. Such carboxylate solutions are also more convenient for processing in terms of ability to dilute or concentrate to an appropriate concentration and viscosity to form a film of the desired density and thickness. In a series of papers, representative ones of which are referenced above, Vest and his colleagues at Purdue University have studied fabrication methods utilizing carboxylate precursors in general and the fabrication of BaTiO$_3$ using such precursors in particular. A the first stage in the process, Vest suggested preparation of neodecanoates as follows:

$$NH_4OH + C_9H_{19}COOH \rightarrow C_9H_{19}COONH_4 + H_2O \quad (8)$$

and $$2C_9H_{19}COONH_4 + BaCl_2 \rightarrow 2NH_4Cl + (C_9H_{19}COO)_2Ba \quad (9)$$

Barium carboxylate is then extracted by xylenes. For titanium, a partially substituted alkoxide derivative was prepared by refluxing titanium methoxide, neodecanoic acid, and methanol to produce the following reaction:

$$Ti(OCH_3)_4 + 2C_9H_{19}COONH \rightarrow (C_9H_{19}COO)_2Ti(OCH_3)_2 + 2CH_3OH \quad (10)$$

with subsequent distilling off of the excess CH$_3$OH. The Ba and Ti derivatives were then combined in xylene at room temperature to form the final precursor used for fabrication of BaTiO$_3$. Vest coined the term "MOD" solutions for such precursors from the fact that after deposition the metal-organics in solution decompose during the drying and annealing processes to form the desired complex metal oxides. The decomposition during the drying and annealing lead to inferior quality films. For example, the carboxylates go through a carbonate stage during the drying and annealing before forming the metal oxide. This can result in some carbonate residue remaining in the final films even after oxygen annealing. Such decompositions make it practically impossible to use the MOD precursors in chemical vapor deposition processes, since the carbon residue coats the substrate.

Turning now to the process of the invention, and using Example 1 above as the exemplary process, barium metal is dissolved in a mixture of 2-ethylhexanoic acid and methoxyethanol, which leads to the alkoxycarboxylate:

$$Ba + 2C_8H_{15}O_2H + CH_3OC_2H_4OH \rightarrow Ba(OC_2H_4OCH_3)_x(C_8H_{15}O_2)_{2-x} \quad (11)$$

where the x value may be 1 or 2. The solution is clear, the brown-red typical of barium methoxyethoxide solutions being absent. However, this does not exclude the formation of barium methoxyethoxide. It only means that the radicals with conjugated bonds which are formed in the process of alkaline oxidation of methoxyethoxide are destroyed in the acidic medium.

After the addition of the strontium, additional 2-ethylhexanoic acid, titanium isopropoxide, and 2-methoxyethanol leads to complex formation immediately, and the subsequent thermal treatment, results in a series of chemical reactions including:

$$Ti(OPr—i)_4 + xC_8H_{15}O_2H \rightarrow Ti(O_2C_8H_{15})_x(OPr—i)_{4-x} + xi—PrOH \quad (12)$$

The complete substitution of alkoxide groups by carboxylates never occurs, which leaves excess 2-ethylhexanoic acid in solution, which takes part in the following reactions:

$$C_8H_{15}O_2H + ROH \leftrightarrow C_8H_{15}O_2R + H_2O \quad (13)$$

and $$ROH + R'OH \leftrightarrow ROR' + H_2O \quad (14)$$

where R=i—Pr, and R'=CH$_3$OC$_2$H$_4$. These reactions result in a gradual elimination of organics from the solution. The different products in the solution during the thermal treatment process is difficult to pinpoint since the process is an on going one, but the fact that a series of products forms is indicated by the gradual and very slow increase of temperature from 79° C. to 116° C. with many steps in temperature in the course of distilling off the organics from the solution. The water that is formed, even if formed in traces, reacts with the alkoxides to form oxoalkoxides, which are believed to be some of the products formed during the thermal treatment process. It is important in the process that the thermal treatment and distillation is performed on the complex solution containing all the metals of the final desired compound, since this insures the metal complex formation in solution. Thus, the true final precursor may be represented as a metal complex such as M$_1$M$_2$O$_x$(OR)$_{y-2x}$(C$_8$H$_{15}$COO)$_{4-y}$, where M$_1$ represents one metal and M$_2$ represents a second metal. In the example of barium titanate, the true final precursor may be represented as $BaTiO_x(OR)_{y-2x}(C_8H_{15}COO)_{4-y}$. Such complexes contain all or most of the metal-oxygen-metal bonds necessary for complex oxide formation on deposition and drying of the final precursor, and in addition the presence of carboxylates preserves the final precursor solution from quick hydrolysis. Thus the result is a final precursor solution that has both the properties of the sol-gels of producing excellent films, and the properties of the MODs of being stable over sufficient periods to enable incorporation into routine manufacturing processes for commercial use.

A feature of the invention is that it uses metal alkoxycarboxylates rather than carboxylates as the initial or intermediate precursor for many metals, and generally also includes alkoxycarboxylates in the final precursor. Another feature of the invention is that in the case of the metal titanium, the isopropoxide is used as the initial precursor, which eliminates the step of titanium alkoxycarboxylate isolation.

Another feature of the invention is that chemical reactions that occur in the precursor preparation stage differ markedly from those of the prior art. These different chemical reactions make an enormous difference in the chemical nature of the final precursor.

A further feature of the invention is the considerable thermal treatment of the combined initial precursors, with complex metal-oxygen-metal bonds being formed during this treatment and thus being present in solution prior to application of the solution to the substrate.

A related feature of the invention is that the complex metal oxide, such as $BaTiO_3$, is formed in one step during the application, drying and heating processes, rather than the precursor compound going through the carbonate stage, such as $BaCO_3+TiO_2$, which requires further thermal treatment after deposition to result in the metal oxide, such as $BaTiO_3$. As a result the metal oxides produced by the process of the invention are microscopically homogeneous and of the high quality necessary in integrated circuit manufacturing processes.

Yet a further feature of the invention is that the precursor contains carboxylate ligands. While the proportion of carboxylate ligands is not as large as in the MOD process, the amount is such that the precursor is stable for periods such as are common for storage of precursors in typical manufacturing processes, i.e. for several months. Thus the precursors and processes of the invention are suitable for large scale commercial fabrication processes.

There has been described novel metal-alkoxocarboxylate precursors and processes utilizing the precursor to fabricate thin films for electronic device applications. It should be understood that the particular embodiments shown in the drawings and described within this specification are for purposes of example and should not be construed to limit the invention which will be described in the claims below. Further, it is evident that those skilled in the art may now make numerous uses and modifications of the specific embodiment described, without departing from the inventive concepts. For example, now that the metal-alkoxocarboxylate precursors have been described, such precursors can be formed by many different perturbations of the specific processes described in the examples. Further, the precursors can be combined with conventional processes to provide variations on the processes described. Other metals may be utilized to form other metal-alkoxocarboxylates. It is also evident that the process steps recited may in some instances be performed in a different order. Or equivalent structures and process may be substituted for the various structures and processes described. Further, now that the advantages of utilizing a precursor in which the metal-oxygen-metal bonds are already formed has been pointed out, many processes utilizing this concept may be devised. Consequently, the invention is to be construed as embracing each and every novel feature and novel combination of features present in and/or possessed by the precursors, precursor formation processes, metal oxide fabrication processes, electronic devices, and electronic device manufacturing methods described.

We claim:

1. A method of making a precursor for fabricating a metal oxide, said method comprising the steps of:

mixing a metal alkoxycarboxylate-containing liquid with a 2-ethylhexanoic acid in an effective amount for shelf-stabilizing said liquid by substituting 2-ethylhexanoate ligands for alkoxide ligands, thereby forming a mixture; and heating said mixture to so substitute said carboxylate ligands for said alkoxide ligands.

2. The method as set forth in claim 1, further including a step of providing said metal alkoxycarboxylate to at least two metals selected from a metal group consisting of barium, strontium, tantalum, calcium, bismuth, lead, yttrium, scandium, lanthanum, antimony, chromium, thallium, titanium, hafnium, tungsten, niobium, zirconlure, manganese, iron, cobalt, nickel, magnesium, zinc, and mixtures thereof.

3. The method as set forth in claim 2, said metals being provided in effective amounts for forming strontium bismuth tantalate upon drying and calcining of said precursor.

4. The method as set forth in claim 2, said metals being provided in effective amounts for forming strontium bismuth niobate upon drying and calcining of said precursor.

5. The method as set forth in claim 2, said metals being provided in effective amounts for forming strontium bismuth tantalum niobate upon drying and calcining of said precursor.

6. The method as set forth in claim 2, said metals being provided in effective amounts for forming barium bismuth tantalate upon drying and calcining of said precursor.

7. The method as set forth in claim 2, said metals being provided in effective amounts for forming lead bismuth tantalate upon drying and calcining of said precursor.

8. The method as set forth in claim 2, said metals being provided in effective amounts for forming barium bismuth niobate upon drying and calcining of said precursor.

9. A precursor produced according to the method of claim 1, said precursor having a shelf life exceeding at least two months.

10. A method of making a barium strontium titanate precursor, said method comprising the steps of:

combining a polyoxyalkylated barium moiety, a polyoxyalkylate strontium moiety, and a polyoxyalkylated titanium moiety to form a liquid solution, each of said respective moieties having a formula in which corresponding barium, strontium, and titanium atoms bond with an oxygen atom in a ligand selected from a ligand group consisting of alkoxides and carboxylates; and heating said liquid solution.

11. The method as set forth in claim 10, wherein said formula defines a member selected from a moiety group consisting of barium carboxylates, barium alkoxides, barium alkoxycarboxylates, strontium carboxylates, strontium alkoxides, strontium alkoxycarboxylates, titanium carboxylates, titanium alkoxides, and titanium alkoxycarboxylates.

12. The method as set forth in claim 11, wherein said heating step includes reacting two members of said moiety group to form a reaction product having a molecular formula including a central oxygen atom connecting two metal atoms, said two members including a single-metal alkoxycarboxylate and a metal alkoxide.

13. The method as set forth in claim 12, said two members including said barium alkoxycarboxylate and said titanium alkoxide.

14. The method as set forth in claim 13, said titanium alkoxide being titanium isopropoxide.

15. A method of making a strontium bismuth tantalate precursor, said method comprising the steps of:

combining a polyoxyalkylated strontium moiety, a polyoxyalkylated bismuth moiety, and a polyoxyalkylated tantalum moiety to form a liquid solution;

each of said respective moieties having a formula in which corresponding strontium, bismuth, and tantalum atoms bond with an oxygen atom in a ligand selected from a ligand group consisting of alkoxides and carboxylates; and heating said liquid solution.

16. The method as set forth in claim 15, wherein said formula defines a member selected from a moiety group consisting of bismuth carboxylates, bismuth alkoxides, bismuth alkoxycarboxylates, strontium carboxylates, strontium alkoxides, strontium alkoxycarboxylates, tantalum carboxylates, tantalum alkoxides, and tantalum alkoxycarboxylates.

17. The method as set forth in claim 16, wherein said heating step includes reacting two members of said moiety group to form a reaction product having a molecular formula including a central oxygen atom connecting two metal atoms, said two members including a single-metal alkoxycarboxylate and a metal alkoxide.

* * * * *